United States Patent

Omatsu et al.

(10) Patent No.: US 10,138,269 B2
(45) Date of Patent: Nov. 27, 2018

(54) METHOD FOR PRODUCING AMINO ACID CRYSTALS AND METHOD FOR PRODUCING PROTEIN CRYSTALS

(71) Applicant: National University Corporation Chiba University, Chiba-shi, Chiba (JP)

(72) Inventors: Takashige Omatsu, Chiba (JP); Katsuhiko Miyamoto, Chiba (JP)

(73) Assignee: NATIONAL UNIVERSITY CORPORATION CHIBA UNIVERSITY, Chiba-shi, Chiba (JP)

( * ) Notice: Subject to any disclaimer, the term of this patent is extended or adjusted under 35 U.S.C. 154(b) by 0 days.

(21) Appl. No.: 15/506,031

(22) PCT Filed: Jul. 27, 2015

(86) PCT No.: PCT/JP2015/071240
§ 371 (c)(1),
(2) Date: Feb. 23, 2017

(87) PCT Pub. No.: WO2016/031463
PCT Pub. Date: Mar. 3, 2016

(65) Prior Publication Data
US 2017/0253630 A1 Sep. 7, 2017

(30) Foreign Application Priority Data
Aug. 31, 2014 (JP) ................................. 2014-176697

(51) Int. Cl.
C03B 7/00 (2006.01)
C07K 1/30 (2006.01)
(Continued)

(52) U.S. Cl.
CPC .............. *C07K 1/30* (2013.01); *C07C 227/42* (2013.01); *C07C 229/08* (2013.01); *C07K 1/306* (2013.01); *C30B 7/00* (2013.01); *C07B 2200/13* (2013.01)

(58) Field of Classification Search
CPC .................................. C30B 7/00; C30B 29/54
See application file for complete search history.

(56) References Cited

U.S. PATENT DOCUMENTS

| 2013/0090459 A1 | 4/2013 | Aslan |
| 2014/0204463 A1 | 7/2014 | Harada et al. |
| 2016/0246001 A1* | 8/2016 | Uchida ............... G02B 6/12011 |

FOREIGN PATENT DOCUMENTS

| JP | 2014-530820 A | 11/2014 |
| WO | WO 2012/169578 A2 | 12/2012 |

(Continued)

OTHER PUBLICATIONS

Garetz et al, "Polarization Switching of Crystal Structure in the Nonphotochemical Light-Induced Nucleation of Supersaturated Aqueous Glycine Solutions", Physical Review Letters vol. 89, No. 17 Oct. 2002 pp. 175501-1 to 175501-4.*

(Continued)

*Primary Examiner* — Robert M Kunemund
(74) *Attorney, Agent, or Firm* — Flynn Thiel, P.C.

(57) ABSTRACT

A method for producing a crystalline amino acid involves a step of irradiating a saturated solution of an amino acid with an optical vortex and depositing a crystalline amino acid in the saturated solution of amino acid.
It is desirable that the amino acid is at least one of alanine, arginine, asparagine, asparagine acid, cysteine, glutamine, glutamine acid, glycine, histidine, isoleucine, leucine, lysine, methionine, phenylalanine, proline, serine, threonine, tryptophan, tyrosine, valine, and derivatives thereof.

5 Claims, 3 Drawing Sheets

(51) Int. Cl.
   *C07C 227/42* (2006.01)
   *C07C 229/08* (2006.01)
   *C30B 7/00* (2006.01)

(56) References Cited

FOREIGN PATENT DOCUMENTS

WO    WO 2013/046257 A1    4/2013
WO    WO 2013/055859 A1    4/2013

OTHER PUBLICATIONS

Jeffries et al "Controlled Shrinkage and Re-expansion of a Single Aqueous Droplet inside an Optical Vortex Trap" J. Phyical Chemistry B 2007 vol. 111 pp. 1806-2812.*

International Search Report tor PCT/JP2015/071240 (2 pgs.).
Polarization Switching of Crystal Structure in the Nonphotochemical Light-Induced Nucleation of Supersaturated Aqueous Glycine Solutions, by B. Garetz et al, Physical Review Letters, 2002, 89(17), English Abstract Only.
Controlled Shrinkage and Re-expansion of a Single Aqueous Droplet Inside an Optical Vortex Trap, by G. Jeffries et al, Journal of Physical Chemistry B, 2007, vol. 111, No. 11, English Abstract Only.
Twisted crystalline silicon nano-cone using optical angular momentum transfer, by S. Takizawa et al, Extended Abstracts, The $61^{st}$ JSAP Spring Meeting, Mar. 2014, p. 04-271 (19p-D1-13), in Japanese and English.
Orbital angular momentum of light and the transformation of Laguerre-Gaussian laser modes, by L. Allen et al, Physical Review A, vol. 45, No. 11, 1992, pp. 8185-8189.

* cited by examiner

METHOD FOR PRODUCING AMINO ACID CRYSTALS AND METHOD FOR PRODUCING PROTEIN CRYSTALS

TECHNICAL FIELD

The present invention relates to a method for producing crystalline amino acids and a method for producing crystal protein.

RELATED ART

An optical Vortex is a light wave which has a characteristic such as angular momentum caused from phase singularity (orbital angular momentum) and doughnut-type intensity distribution.

A typical example of optical vortex is a Laguerre-Gaussian beam (see above-mentioned non-patent document 1).

A Laguerre-Gaussian beam is an intrinsic solution of a wave equation in cylindrical coordinates system. It satisfies a boundary condition in which the phase rotates by an integral multiple of 2 pi when it propagates one wavelength around a rotation center.

Thus, the orbital angular momentum can be expressed by using a quantum number L (L=1, 2, 3 . . . ).

The wave surface of an optical vortex is helical, and the orbital angular momentum works along the direction which is given by the difference vector between the direction of a normal direction and the propagation direction of the light.

An optical vortex can be used for an optical manipulation which uses the light radiation pressure, a microscope with a high resolution which uses the phase singularity, and a light ablation processing which initiatively uses the orbital angular momentum. Thus, an industrial application of an optical vortex is very expected.

As a known art of generating an optical vortex, there is a machine which is described in the below-described patent document 1 and non-patent document 1.

REFERENCE FOR RELATED ART

Patent Document patent document 1 WO2012/169578

Non-Patent Document non-patent document 1
L. Allen, M. W. Beijersbergen, R. J. C. Spreeuw, and J. P. Woerdman, "Orbital angular momentum of light and the transformation of Laguerre-Gaussian laser modes", Phys. Rev. A 45, 8185-8189 (1992)

DESCRIPTION OF THE INVENTION

Problems to be Solved by the Invention

However, the arts, which are described in patent document 1 and non-patent document 1, are only focused on a method for generating an optical vortex. Therefore, there remains a problem to be considered in the industrial application of optical vortexes such as the above-mentioned optical manipulation.

Accordingly, with the consideration of the above-mentioned problem, an object of the present invention is to provide a new application of optical vortexes.

Solution to the Problem

By examination with regard to the above-mentioned problems, the inventors found that a crystalline amino acid or a protein crystal can be produced when an optical vortex is irradiated to a saturated solution of an amino acid or a saturated solution of protein.

Accordingly, one aspect of the present invention is a method for producing a crystalline amino acid comprises a step of irradiating a saturated solution of an amino acid with an optical vortex, and depositing a crystalline amino acid in the saturated solution of the amino acid.

Further, in the aspect, it is desirable that the amino acid contains at least one of alanine, arginine, asparagine, asparagine acid, cysteine, glutamine, glutamine acid, glycine, histidine, isoleucine, leucine, lysine, methionine, phenylalanine, proline, serine, threonine, tryptophan, tyrosine, valine, and derivatives thereof. However, it is not limited to those.

Further, in this aspect, it is desirable that the optical vortex is a circularly polarized light.

Moreover, another aspect of the present invention is a method for producing a crystal protein, which comprises a step of irradiating a saturated solution of protein with an optical vortex, and depositing a crystal protein in the saturated solution of protein.

Further, in this aspect, it is desirable that the optical vortex is a circularly polarized light.

Effects of the Invention

As a result from the above, by the present invention, it is possible to provide a new application of an optical vortex.

Further, the crystalline amino acid and the protein crystal have a high single crystallinity, and it is possible to produce the crystal much faster than previously known.

Then, it is expected to produce a great benefit in the fields of medicine, chemistry, feed, and food.

BEST MODE FOR CARRYING OUT THE PRESENT INVENTION

Hereinafter, embodiments and examples of the present invention are described with reference to the drawings. However, the present invention can be accomplished with different embodiments and is not limited to the embodiments or examples described below.

A method for producing a crystalline amino acid of this embodiment comprises a step of irradiating a saturated solution of an amino acid with a circular polarized optical vortex, and depositing a crystalline amino acid in the saturated solution of the amino acid.

In this embodiment, as mentioned-above, "optical vortex" means a light wave which has a characteristic such as angular momentum caused from phase singularity (orbital angular momentum) and doughnut-type intensity distribution.

Figure 1:
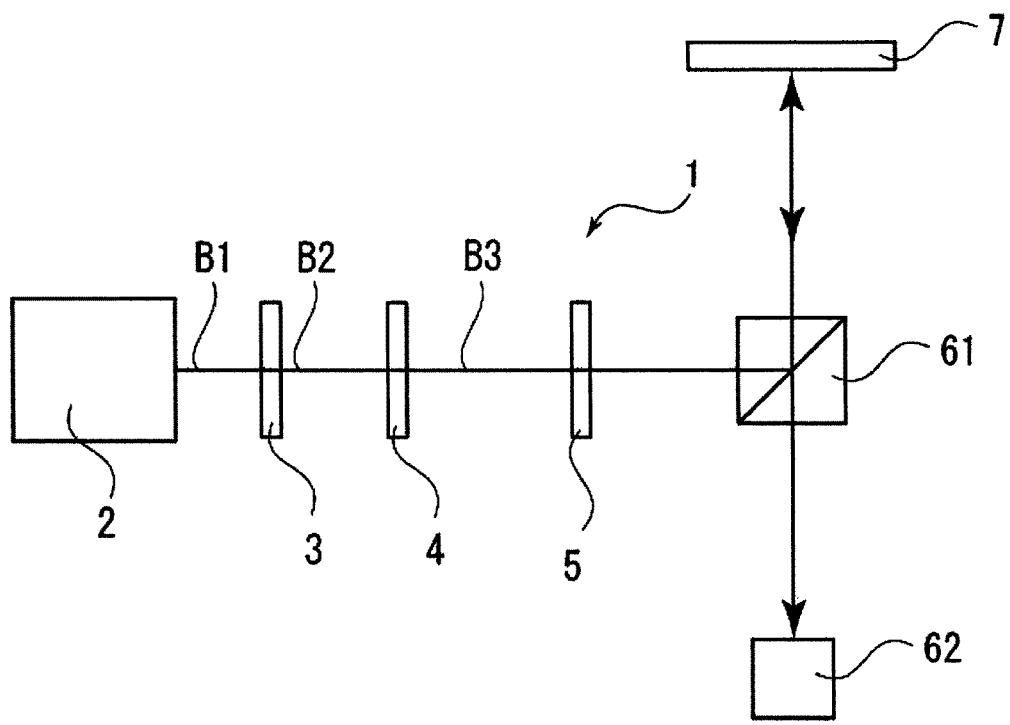
FIG. 1 shows a schematic view of an optical vortex laser generator of the embodiment, which generates an optical vortex.

It is desirable that the way for generating the optical vortex is to use an optical vortex laser device (hereafter referred as to "the laser device") which is as shown in FIG. 1, but is not limited to that.

Here, FIG. 1 shows a schematic view of the optical system of an optical vortex laser device of this embodiment (hereafter referred as to "the laser device") 1.

As shown in this figure, the laser device 1 has a laser source 2 which emits laser light B1, an optical vortex generating unit 3 which generates optical vortex B2 based on the laser light B1 which is emitted from the laser source 2, a quarter wave plate 4 which generates a circular polarized optical vortex B3 based on the optical vortex B2 which is generated by the optical vortex generating unit 3, and a light condensing unit 5 which concentrates the circular polarized optical vortex.

In this embodiment, as described above, the laser source 2 emits a laser light B2.

It is desirable that the laser source 2 is a solid state laser such as a YAG laser, a dye laser, a gas laser such as a He—Ne laser, or a semiconductor laser such as a LD laser. But it is not limited to that.

However, it is desirable that the range of the wavelength of the laser light which the laser light source 2 emits is the range that the object to be irradiated can occur a photoisomerization reaction. Further, it is desirable that the range of the wavelength of the light is in from ultraviolet region to infrared region. Specifically, it is more desirable that the wavelength is from 350 nm to 1.3 μm. It is adjustable by selecting appropriate material.

Moreover, in this embodiment, it is desirable that the laser source 2 is a continuous oscillating laser light source which can emit continuous wave laser light.

By using continuous wave laser light, it is possible to keep irradiating an optical vortex to a polymer.

Incidentally, it is possible to use a pulsed laser. However, in this case, it is desirable that the repetition frequency is sufficiently high so that the photoisomerization can be maintained.

Moreover, in this embodiment, the optical vortex generating unit 3 is used for generating an optical vortex B2 from the laser light B1 which is emitted from the laser source 2.

It is desirable that the optical vortex generation unit 3 is a phase plate, a spatial phase modulator, or a multimode area fiber amplifier, but is not limited to those.

Moreover, it is desirable that the optical vortex generation unit 3 is integrated with the laser source 2 and generates the optical vortex directly.

It is more desirable that the optical vortex is a coherent optical vortex.

In this embodiment, the quarter wave plate 4 is used for changing the optical vortex into circular polarized light B3.

If the optical vortex laser generating unit 3 can generate circular polarized light, the quarter wave plate 4 can be omitted.

In this embodiment, by the quarter wave plate 4, it is possible to form a crystalline amino acid in a saturated solution of the amino acid.

Moreover, in this embodiment, the light condensing unit 5 is used for concentrating the light and irradiating the light on the surface of a saturated solution of the amino acid.

It is desirable that the light condensing unit 5 contains a microscope objective lens, and is not limited to that as long as it is possible for the circular optical vortex to be irradiated efficiently. Then, the beam diameter can be adjusted by the microscope objective lens.

Moreover, in this embodiment, it is desirable that the laser device has an observation unit 6.

Further, it is desirable that the observation unit 6 has a beam splitter 61, which splits the optical vortex condensed by the light condensing unit 5 into two lights, and an imaging unit 62, which observes the light reflected from the saturated solution of the amino acid but is not limited to that.

It is desirable that the imaging unit 62 is a CCD camera. Further, it is desirable that image processing is performed by using the CCD camera and a data processing apparatus such as a personal computer, connected to each other.

Moreover, in this embodiment, "amino acid" means an organic compound which has an amino group and a carboxyl group, and it includes a compound and a derivative of it, which constitutes a protein of a living organism.

An example of an amino acid which constitutes a protein of a living organism is alanine, arginine, asparagine, asparagine acid, cysteine, glutamine, glutamine acid, glycine, histidine, isoleucine, leucine, lysine, methionine, phenylalanine, proline, serine, threonine, tryptophan, tyrosine, or valine, but is not limited to these.

Moreover, in this embodiment, "saturated solution of amino acid" means a solution in which the amino acid is dissolved up to its solubility level.

In the case that many amino acids can be dissolved in the solution, it is necessary that at least one amino acid is dissolved in a saturated state but it is desirable that all of the amino acids are dissolved in a saturated state.

Further, pure water is desirable as a solvent for dissolving the amino acid. However, it is not limited as long as it can dissolve the amino acid.

Moreover, in this embodiment, it is desirable that the energy of the optical vortex is within an appropriate range. Because if the energy of the optical vortex is too small, a crystalline amino acid cannot be formed, and if it is too high, the crystallinity of the crystalline amino acid may be lower.

The desirable range of the energy of the optical vortex is from 1 W to 1.5 W, but it is not limited that and it is adjustable according to material.

Moreover, in this embodiment, the irradiation time of the optical vortex is adjustable so long as the crystal can be formed.

Especially, in this embodiment, it is possible to form a crystal with a high single crystallinity in a very short time such as about a few tens of seconds.

In this embodiment, it is possible to form the crystalline amino acid in a saturated solution of the amino acid by irradiating the optical vortex into the saturated solution. Specifically, it is possible to form the crystalline amino acid with a high crystallinity (single crystal, crystal structure).

The working mechanism of forming the crystalline amino acid in the solution is not currently clear.

However it is thought that a core can be formed by radiating the optical vortex, the orbital motion of the core makes the concentration in the solution uniform, and the crystallinity of the crystalline amino acid can dramatically be higher.

As a result from the above, by the embodiment of the present invention, it is possible to provide a new application of an optical vortex.

Further, the crystalline amino acid has a high single crystallinity, and it is possible to produce the crystal much faster than known arts.

Then, it is expected to produce a great benefit in the fields of medicine, chemistry, feed, and food.

Further, in this embodiment, the amino acid was described as an example. But a protein can be used as an example the same as the amino acid.

When a protein is used, each "amino acid" in the above description is to be read as "protein".

Further, in the case of a protein, for example, lysozyme is desirable.

Furthermore, the crystallization with a high crystallinity of an organic compound, which shows a non-linearity, such as N,N-diethylaminosulfur trifluoride (DAST) is expected.

Example

The effect of the present invention was confirmed by the experiment below. The detail will be described as below.
(Glycine Saturated Deuterium Oxide Solution)

Nd:YVO$_4$ laser whose center wavelength is 1064 nm, spiral phase plate (SPP), quarter wave plate and an objective lens (NA-0.65) were used in the optical system shown in FIG. 1.

Then, the light was irradiated to a saturated deuterium oxide solution in which glycine was dissolved up to its solubility limit via the components.

The diameter of the laser spot which was radiated to the amino acid saturated deuterium oxide solution was (Ppm.

The direction of the circular-polarized light and the wave surface of the optical vortex was set in the same direction.

The total angular momentum (J=1+s) of the circularly-polarized optical vortex, which is the sum of the orbital angular momentum
(l=−1 or 1) and the spin angular momentum (s=−1 or 1), was changeable.

Then, a crystalline amino acid was produced in the saturated amino acid deuterium oxide solution.

Figure 2:
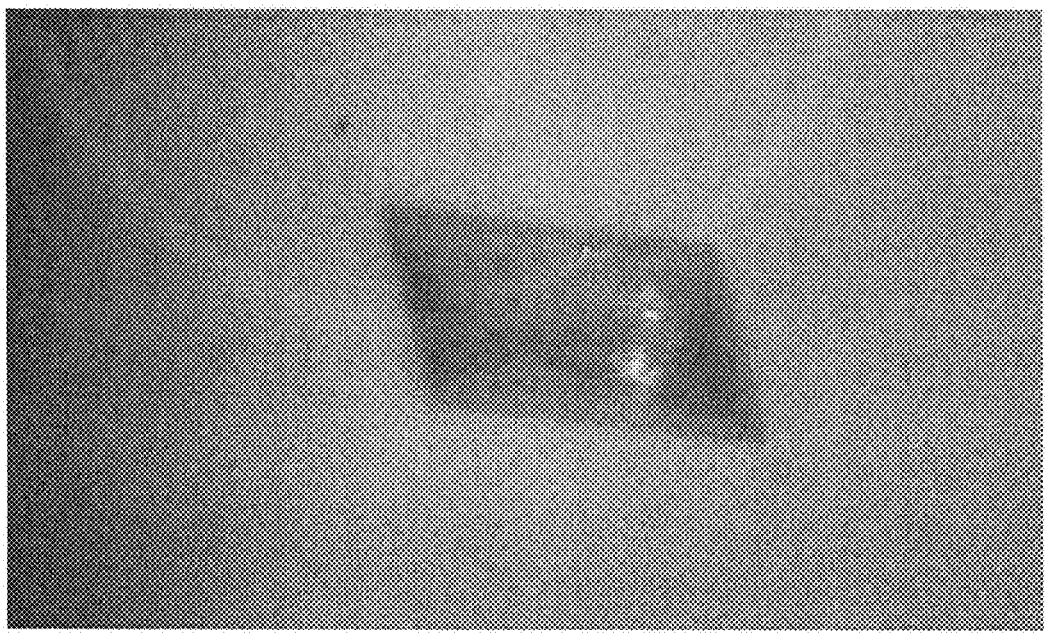
FIG. 2 shows a photographic view of a glycine crystal of an example of the present invention.

The result is shown in FIG. 2.

As a result, a crystalline amino acid deposition immediately began after irradiating with the optical vortex. Then, an alpha-type crystal of glycine, whose size is 1 mm×1 mm, was obtained in about a few tens of seconds from the start of irradiation.

The plane direction mosaic was 0.5, and a crystal with a very high crystallinity was obtained.

Comparison Example

Generating a crystalline amino acid was tried in the same condition with the above example of glycine except for using a linear polarized Gaussian beam laser light.

Figure 3:
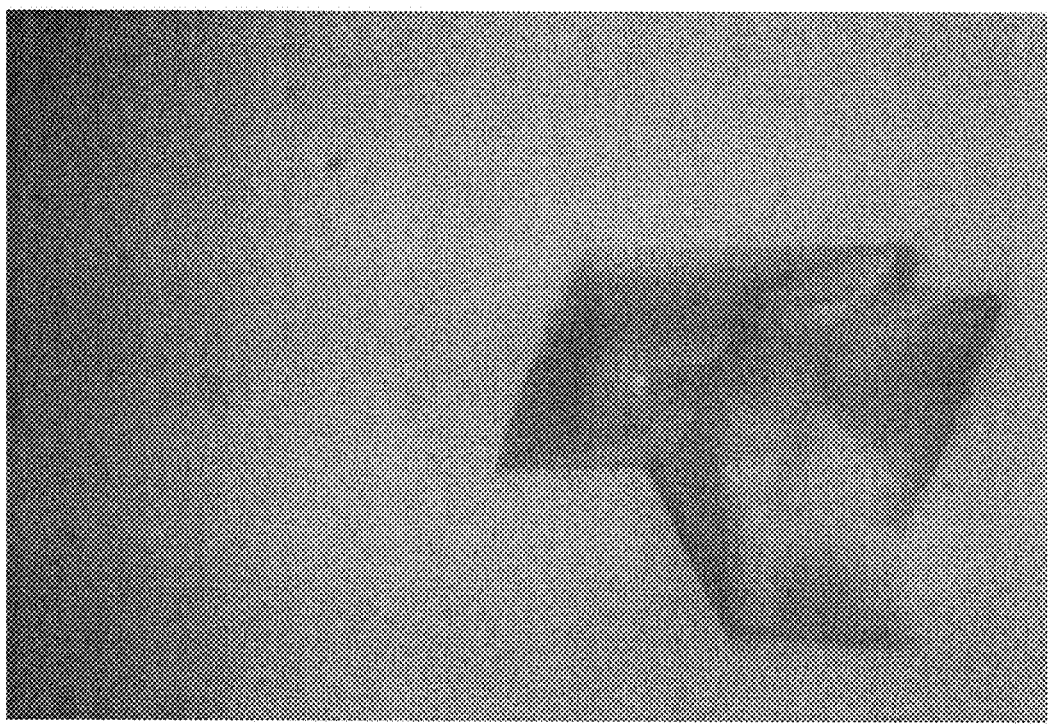
FIG. 3 shows a photographic view of a glycine crystal of a comparative example.

The result is shown in FIG. 3.

In this result, the amino acid was educed, but it was polycrystalline.

INDUSTRIAL APPLICABILITY

The present invention is industrially applicable as a method for producing a crystalline amino acid and a protein crystal.

What is claimed is:

1. A method for producing a single crystalline amino acid comprising:
   a step of irradiating a saturated solution of an amino acid with a circularly polarized optical vortex, and depositing the crystalline amino acid in said saturated solution of amino acid.

2. The method for producing the single crystalline amino acid according to claim 1,
   wherein said amino acid comprises at least one member selected from the group consisting of alanine, arginine, asparagine, asparagine acid, cysteine, glutamine, glutamine acid, glycine, histidine, isoleucine, leucine, lysine, methionine, phenylalanine, proline, serine, threonine, tryptophan, tyrosine, valine, and derivatives thereof.

3. A method for producing a single crystal protein, comprising:
   a step of irradiating a saturated solution of protein with a circularly polarized optical vortex, and depositing the crystal protein in said saturated solution of protein.

4. The method for producing the single crystalline amino acid according to claim 1,
   wherein the range of energy of said circularly polarized optical vortex is from 1-1.5 W.

5. The method for producing the single crystal protein according to claim 3,
   wherein the range of energy of said circularly polarized optical vortex is from 1-1.5 W.

* * * * *